United States Patent
Lin et al.

(10) Patent No.: US 10,682,113 B2
(45) Date of Patent: Jun. 16, 2020

(54) SELF-CALIBRATING DEVICE FOR X-RAY IMAGING SCANNERS

(71) Applicant: Carestream Health, Inc., Rochester, NY (US)

(72) Inventors: Yuan Lin, Rochester, NY (US); William J. Sehnert, Fairport, NY (US)

(73) Assignee: Carestream Health, Inc., Rochester, NY (US)

(*) Notice: Subject to any disclaimer, the term of this patent is extended or adjusted under 35 U.S.C. 154(b) by 417 days.

(21) Appl. No.: 15/461,600

(22) Filed: Mar. 17, 2017

(65) Prior Publication Data
US 2018/0070912 A1 Mar. 15, 2018

Related U.S. Application Data
(60) Provisional application No. 62/394,234, filed on Sep. 14, 2016.

(51) Int. Cl.
*A61B 6/08* (2006.01)
*A61B 6/00* (2006.01)
(Continued)

(52) U.S. Cl.
CPC .............. *A61B 6/547* (2013.01); *A61B 6/025* (2013.01); *A61B 6/107* (2013.01); *A61B 6/12* (2013.01);
(Continued)

(58) Field of Classification Search
CPC .... A61B 2034/2051; A61B 2090/3966; A61B 2090/397; A61B 2090/3995; A61B 6/025; A61B 6/107; A61B 6/4405; A61B 6/547; A61B 6/4233; A61B 6/4283; A61B 6/4411; A61B 6/56; A61B 6/12; A61B 90/39; A61B 1/3132; A61B 2034/2048; A61B 2034/2057; A61B 2090/376; A61B 2090/378; A61B 2090/3782; A61B 34/20; A61B 6/4417; A61B 6/4441; A61B 6/487; A61B 2017/00867; A61B 17/0401; A61B 2017/0409; A61B 2017/0417; A61B 2017/0419; A61B 2017/0496; A61B 17/06066; A61B 17/29; A61B 2017/06052; A61B 2017/3488; A61B 17/0469;
(Continued)

(56) References Cited

U.S. PATENT DOCUMENTS 5,359,637 A * 10/1994 Webber .................. A61B 6/025
378/162
5,668,844 A 9/1997 Webber
(Continued)

FOREIGN PATENT DOCUMENTS

WO 2016/003957 A2 1/2016

*Primary Examiner* — Irakli Kiknadze (57) ABSTRACT

A position sensor has one or more fiducials formed of radio-opaque material and mounted along a surface of a radio-translucent body. A sensor element is coupled to the radio-translucent body and is spaced apart from the one or more fiducials and is energizable to acquire image content during receipt of exposure energy from an X-ray source to the position sensor. The sensor element is in signal communication with a processor and is energizable to generate data that is indicative of a relative position of the X-ray source. A radio-opaque covering is coupled against an outer surface of the radio-translucent body.

14 Claims, 9 Drawing Sheets

(51) Int. Cl.
   *A61B 6/12* (2006.01)
   *A61B 90/00* (2016.01)
   *A61B 6/02* (2006.01)
   *A61B 6/10* (2006.01)
   *G01D 18/00* (2006.01)
   *A61B 34/20* (2016.01)

(52) U.S. Cl.
   CPC ............ *A61B 6/4405* (2013.01); *A61B 90/39* (2016.02); *A61B 2034/2051* (2016.02); *A61B 2090/397* (2016.02); *A61B 2090/3966* (2016.02); *A61B 2090/3995* (2016.02)

(58) Field of Classification Search
   CPC ..... A61B 17/0487; A61B 17/08; A61B 17/10; A61B 2017/0404; A61B 2017/0445; A61B 2017/0446; A61B 2017/045; A61B 2017/0451; A61B 2017/0454; A61B 6/06; A61B 6/542; A61B 6/587; A61B 6/032; A61B 6/4291; A61B 6/469; A61B 6/488; A61B 6/4452; A61B 6/4476; A61B 6/484; A61B 6/545; A61B 6/4464; A61B 6/461; A61B 6/467; A61B 6/4258; A61B 6/5205; A61B 6/037; A61B 6/03; A61B 5/055; A61B 8/4245; A61B 34/10; A61B 5/489; A61B 90/37; A61B 2090/374; A61B 2090/3762; A61B 5/4528; A61B 6/548; A61B 6/14; A61B 6/5258; A61B 6/563; A61B 6/4208; A61B 6/4488; A61B 6/54; A61B 18/1492; G01T 1/02; G08B 21/18; G21K 1/10; A61J 15/0049; A61J 15/0084; A61J 15/0088
   USPC ............... 378/205, 207, 19, 98.8, 70, 86–90
   See application file for complete search history.

(56) References Cited

U.S. PATENT DOCUMENTS

| | | | |
|---|---|---|---|
| 6,471,399 B1* | 10/2002 | Zylka | A61B 6/583 |
| | | | 378/207 |
| 10,285,656 B2* | 5/2019 | Wang | A61B 6/4405 |
| 2008/0095302 A1 | 4/2008 | Ruhrnschopf et al. | |
| 2014/0185762 A1* | 7/2014 | Lee | G01N 23/04 |
| | | | 378/62 |
| 2016/0135764 A1* | 5/2016 | Wojcik | A61B 6/4233 |
| 2016/0296293 A1* | 10/2016 | Gill | A61B 34/30 |

* cited by examiner

SELF-CALIBRATING DEVICE FOR X-RAY IMAGING SCANNERS

CROSS REFERENCE TO RELATED APPLICATIONS

This application claims the benefit of U.S. Provisional application U.S. Ser. No. 62/394,234, provisionally filed on Sep. 14, 2016, entitled "SELF-CALIBRATING DEVICE FOR X-RAY IMAGING SCANNERS" in the names of Yuan Lin and William J. Sehnert, incorporated herein in its entirety.

TECHNICAL FIELD

This disclosure relates, in general, to medical imaging modalities such as radiography, computed tomography (CT), tomosynthesis, cone beam computed tomography (CBCT), dual-energy CT, and the like. In particular, the disclosure relates to a device that can be coupled to an X-ray detector in order to automatically calibrate the geometry of the imaging system.

BACKGROUND

Having precise geometric information for components of an imaging system, such as the positional coordinates and orientation of the X-ray detector and locations of the X-ray tube and X-ray detector, is a basic requirement for obtaining accurate data content, particularly affecting the image quality of reconstructed images. Mismapping between the intended object space and projection images can degrade spatial resolution and can lead to various types of image artifacts, such as ring artifacts.

The spatial geometry of the imaging system can be well-defined when using stationary imaging scanners and scanning apparatus that fix the position of the X-ray source and detector, such as using a C-arm or other mounting mechanism. Where this geometry is fixed by the imaging system, geometric calibration is straightforward and can be performed at periodic intervals using a calibration phantom.

However, with the introduction of portable and mobile digital X-ray imaging apparatus, the problem of geometric calibration becomes more acute. When used with bedridden patients, for example, it can be necessary to manually position the detector behind the patient and to determine the relative position of the X-ray source to the detector. Accurate calculation of the geometry of the imaging components is needed in order to obtain the best possible image quality under these challenging conditions, both for conventional 2-D radiography and for 3-D image reconstruction imaging, such as for tomosynthesis, computed tomography (CT), and cone-beam computed tomography (CBCT) imaging. With manual positioning of the source and detector components and the need for correlating the position of these devices to each other, each imaging exam requires separate geometric calibration.

It should be noted that calibration apparatus and methods should not compromise image quality, the mechanical integrity and usability of the detector, or protective features that eliminate or significantly reduce the likelihood of stray radiation.

It can thus be appreciated that there is a need for automated calibration apparatus and methods to support portable radiographic imaging apparatus.

The background above is provided for general overview information and is not intended to be used as an aid in determining the scope of the claimed subject matter. The invention is defined by the claims.

SUMMARY

Certain embodiments described herein address the need for geometric calibration of radiographic imaging apparatus that provide either or both 2-D radiography and 3-D imaging. To overcome limitations of existing approaches, the present disclosure describes a calibration apparatus and method that can help to provide information on relative spatial coordinates for the radiation source and the digital radiography detector. Advantageously, the calibration approach described herein allows use of an automated calibration sequence that can be executed as part of the image acquisition sequence. The proposed solution of the present disclosure provides apparatus and methods for geometric calibration that do not compromise image quality or the mechanical integrity and usability of the detector, or obstruct operation of protective features for limiting the risk of unintended x-ray exposure.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a position sensor comprising: one or more fiducials formed of radio-opaque material and mounted along a surface of a radio-translucent body; a sensor element that is coupled to the radio-translucent body and that is spaced apart from the one or more fiducials and is energizable to acquire image content during receipt of exposure energy from an X-ray source and to generate a signal according to the acquired image content, wherein the sensor element is in signal communication with a processor that is energizable to generate data that is indicative of a relative position of the X-ray source; and a radio-opaque covering that is coupled against outer surfaces of the radio-translucent body.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

The following is a detailed description of the embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the object that is imaged, such as the "subject patient", for example.

Radio-opaque materials provide sufficient absorption of X-ray energy so that the materials are distinctly perceptible within the acquired image content. Radio-translucent or transparent materials are imperceptible or only very slightly perceptible in the acquired radiographic image content.

In the context of the present disclosure, "volume image content" describes the reconstructed image data for an imaged subject, generally stored as a set of voxels. Image display utilities use the volume image content in order to display features within the volume, selecting specific voxels that represent the volume content for rendering a particular slice or view of the imaged subject. Thus, volume image content is the body of resource information that is obtained from a radiographic or other volume imaging apparatus such as a CT, CBCT, MDCT, MRI, PET, tomosynthesis, or other volume imaging device that uses a reconstruction process and that can be used to generate depth visualizations of the imaged subject.

Examples given herein that may relate to particular anatomy or imaging modality are considered to be illustrative and non-limiting. Embodiments of the present disclosure can be applied for both 2D radiographic imaging modalities, such as radiography, fluoroscopy, or mammography, for example, and 3D imaging modalities, such as CT, MDCT, CBCT, tomosynthesis, dual energy CT, or spectral CT.

In the context of the present disclosure, the term "volume image" is synonymous with the terms "3 dimensional image" or "3D image".

In the context of the present disclosure, a radiographic projection image, more simply termed a "projection image" or "x-ray image", is a 2D image formed from the projection of x-rays through a subject. In conventional radiography, a single projection image of a subject can be obtained and analyzed. In volume imaging such as CT, MDCT, and CBCT imaging, multiple projection images are obtained in series, then processed to combine information from different perspectives in order to form image voxels.

Two different types of calibration sequences are typically used to maintain a radiographic imaging apparatus such as a CBCT or tomosynthesis system in order to obtain acceptable imaging quality:

(i) quantitative calibration, for measuring and calibrating system response according to Hounsfield values that relate to radiation density and absorption. This type of calibration uses calibration phantoms having regions of different relative density.

(ii) geometric calibration that maintains pixel-by-pixel registration for each acquired image and compensates for mechanical drift and shifting due to weight, movement, and other factors.

Embodiments of the present disclosure are directed to apparatus and methods for geometric calibration (ii), providing solutions that can be particularly useful with volume imaging apparatus such as a CBCT system.

Reference is made to U.S. Pat. No. 5,668,844 (Webber) titled SELF-CALIBRATED TOMOSYNTHETIC, RADIO-GRAPHIC-IMAGING SYSTEM, METHOD, AND DEVICE, incorporated herein by reference in its entirety.

Figure 1:
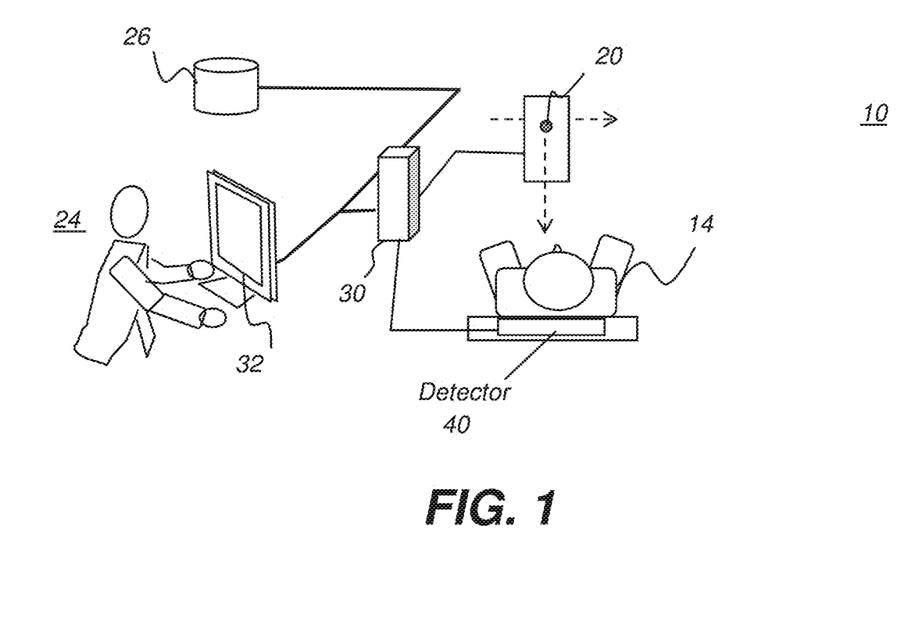
FIG. 1 is a schematic diagram that shows an imaging apparatus for obtaining X-ray images.

The schematic diagram of FIG. 1 shows an imaging apparatus 10 for acquiring radiographic images of a patient 14 for tomosynthesis using a portable digital radiography (DR) detector 40. DR detector 40 is manually positioned behind patient 14 or other subject relative to an X-ray source 20 that can be energized to direct radiation toward the subject. In the embodiment shown, X-ray source 20 scans over a short distance from left to right to obtain multiple images for depth or volume reconstruction. A processor 30, such as a computer or other control logic processor, in signal communication with a memory 26, is energizable to control and coordinate energizing X-ray source 20 and acquiring image data from detector 40. Processor 30 can also generate the reconstructed image content, presented to a practitioner 24 on a display 32.

Figure 2:
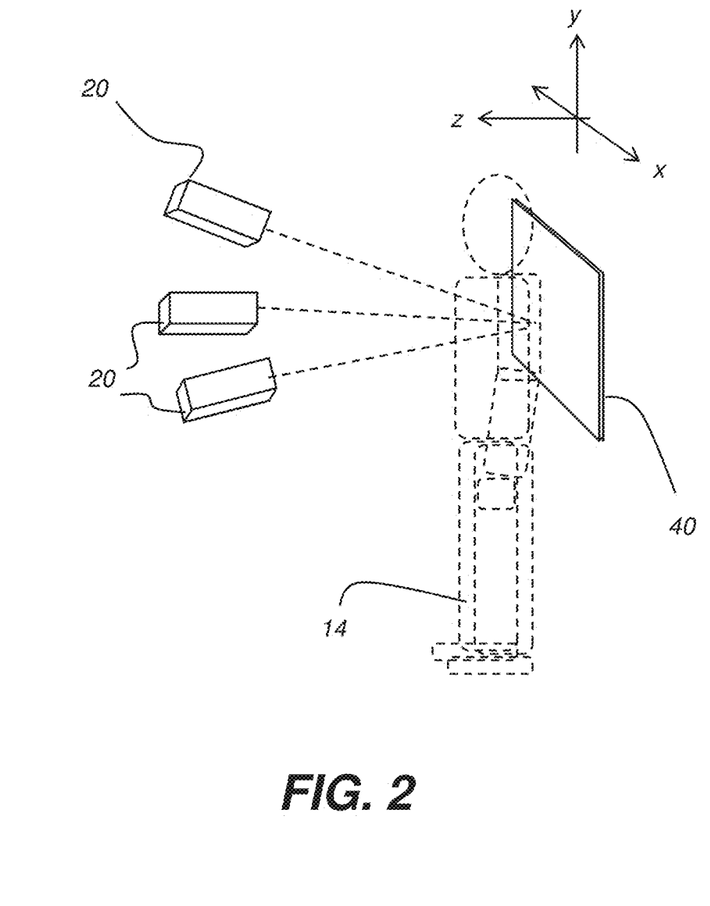
FIG. 2 is a schematic diagram that shows why identifying the position of source relative to detector is beneficial.

In addition to manual positioning of the DR detector 40, portable imaging apparatus may also require manual positioning of X-ray source 20. The schematic diagram of FIG. 2 shows why identifying the position of source 20 relative to detector 40 is particularly beneficial for accurate imaging and reconstruction. Where a single radiographic image is acquired, the relative angle and position of source 20 changes the path of radiation through the subject, shown as patient 14, providing different information on subject anatomy and density according to the angle. Where multiple projection images are obtained, such as for tomosynthesis or CBCT, the angular orientation must be known with some accuracy in order to provide useful data for volume or depth reconstruction.

Figure 3:
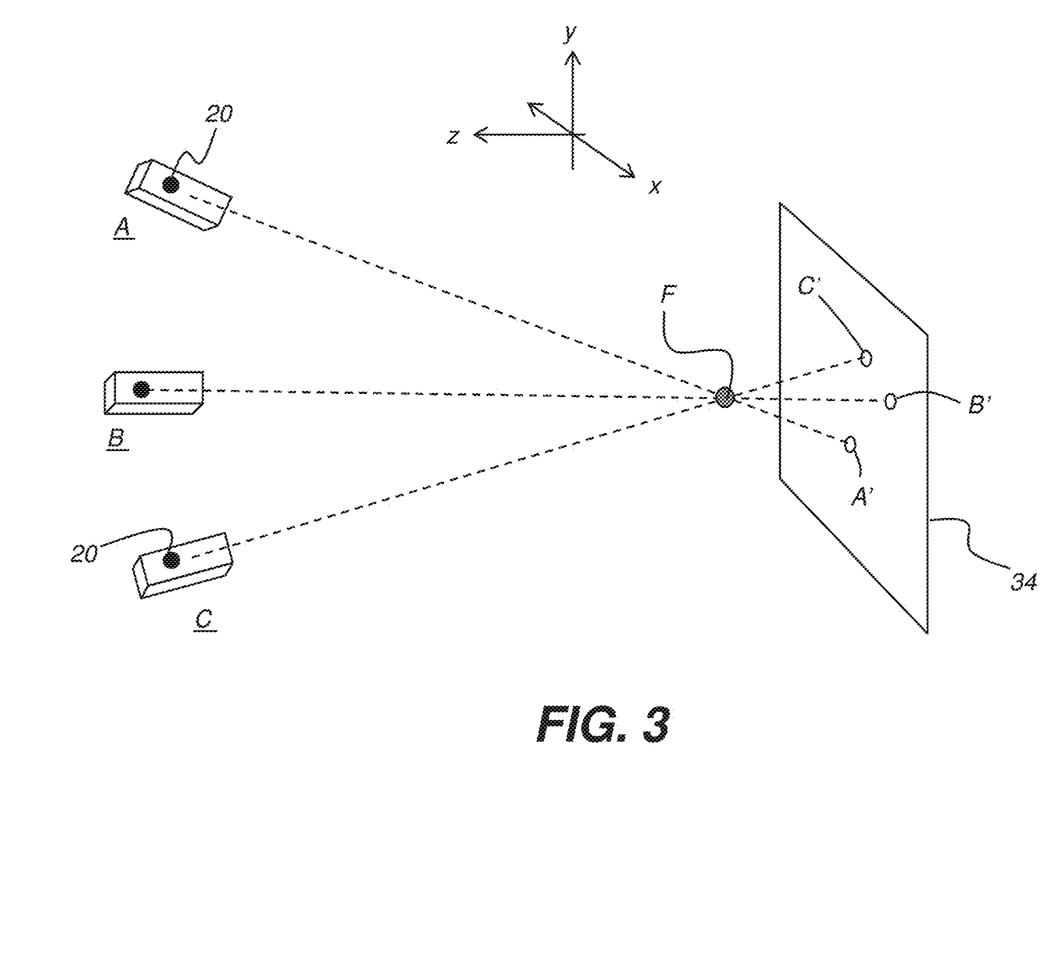
FIG. 3 is a schematic diagram that shows how the fiducial of the present disclosure indicates different relative angles of source to detector.

Embodiments of the present disclosure address the problem of geometric calibration of source 20 to detector 40 using fiducials and sensing apparatus positioned in the path of radiation energy. Detector 40 can be any size, such as a full size Digital Radiation (DR) detector, for example. The schematic diagram of FIG. 3 shows, in exaggerated form, how a radio-opaque fiducial F and an area sensor element 34 can be used to show the relative angle of the X-ray source 20 to the detector, relative to the x, y, z axes shown. Sensor element 34 is an area sensor that is responsive to radiation energy. Fiducial F is a radio-opaque element that absorbs radiation energy from source 20, located in different relative positions in FIG. 3, shown as positions A, B, and C. The resulting imaged content, formed as the shadow of fiducial F, is measured at corresponding respective positions A', B', and C' on sensor element 34; the relative position of the shadow of the fiducial F is indicative of the angle of the source 20 to sensor element 34. The resulting signals from the sensor element 34 are thus indicative of the relative angle of the source 20.

Embodiments of the present disclosure detect the relative source 20 to DR detector 40 position by triangulation that combines the angular data shown in the FIG. 3 example for multiple fiducials, spaced apart from each other along the imaging plane of the DR detector. The schematic diagram of FIG. 4 shows the use of two fiducials F1 and F2 for obtaining source 20 relative position data.

Fabrication and Configuration of Sensor

Figure 4:
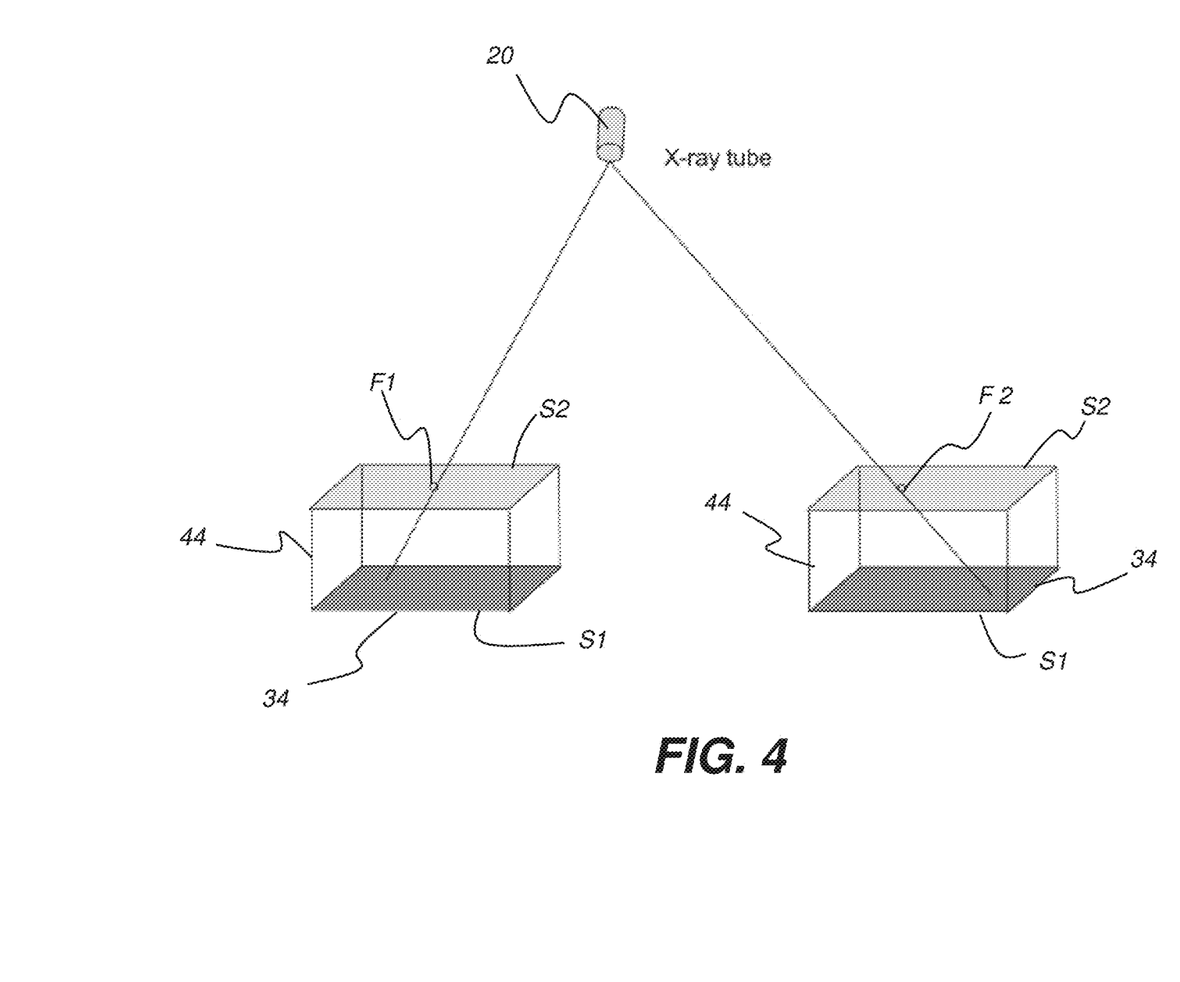
FIG. 4 is a schematic diagram that shows sensing X-ray source position using two position sensors.
Figure 5:
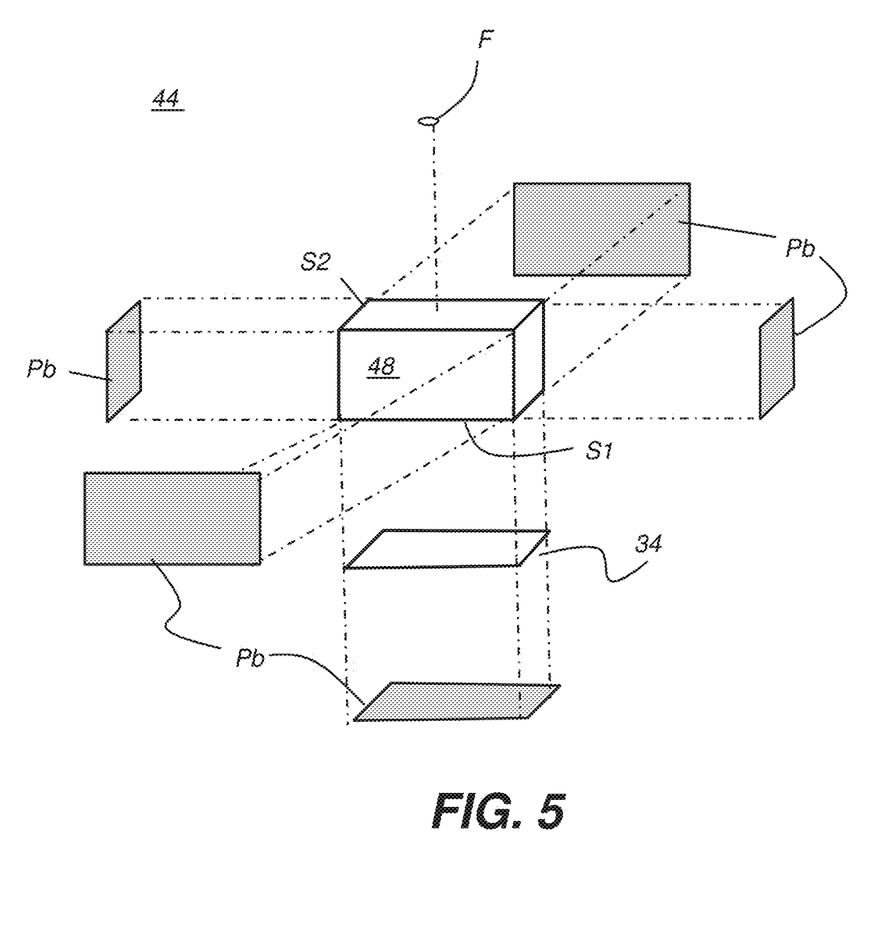
FIG. 5 is an exploded view that shows components of a position sensor according to an embodiment of the present disclosure.

Referring to FIG. 4 and the exploded view of FIG. 5, each fiducial F, F1, F2 is part of a position sensor 44 that includes the fiducial mounted at a fixed distance from sensor element 34. According to an embodiment of the present disclosure, position sensor 44 is formed from a body or block 48 of X-ray translucent material, such as an acrylic or other plastic material. High-resolution sensor element 34 lies against one surface 51 of block 48; the fiducial F1 is applied to or embedded on the surface or within the block of material near the opposite surface S2, which serves as an incident surface and is radio-translucent. All surfaces except incident surface S2 can be treated to be radio-opaque, such as by wrapping or coating with lead or other radio-opaque material Pb. Treatment of surfaces to be radio-opaque helps to reduce backscatter from the received radiation.

Figure 6:
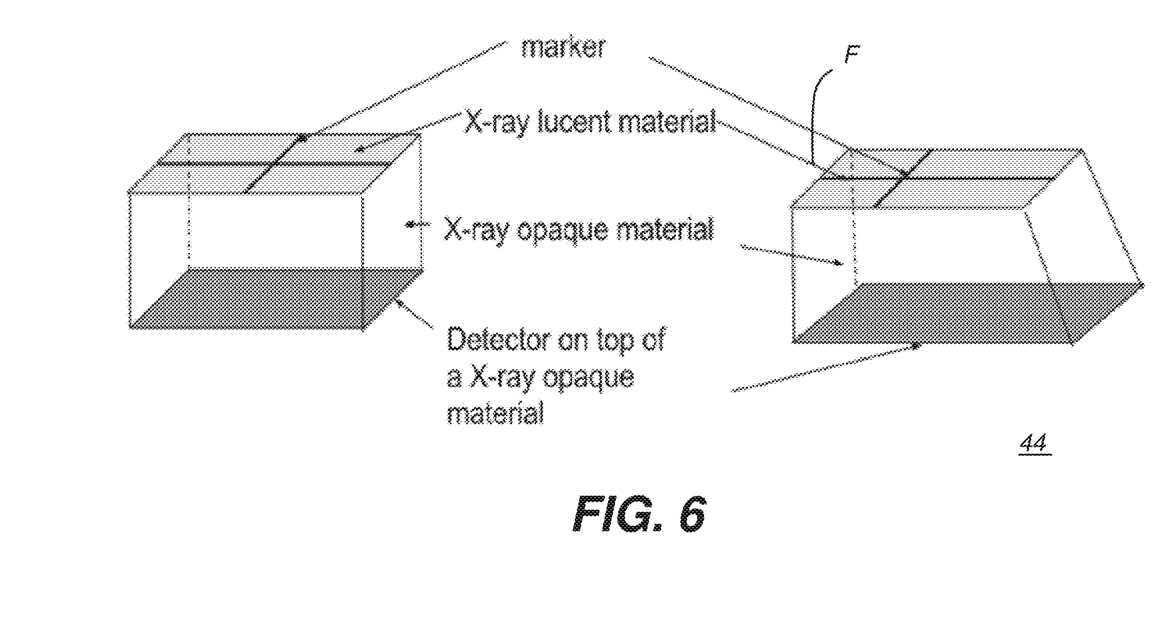
FIG. 6 is a perspective view that shows the position sensor with an alternate arrangement of the fiducial.

FIG. 6 shows the use of an alternate fiducial F such as a cross or other marker for identifying fiducial location as part of position sensor 44. Radio-opaque wires or deposited radio-opaque materials can be used to provide the type of marker shown as fiducial F in FIG. 6 or other type of fiducial pattern.

Radio-lucent materials used for position sensor 44 can include various types of fiber-reinforced plastics, such as carbon fiber-reinforced plastics. Thermoplastic materials can be used. Position sensor 44 can contain air or other gaseous material.

The shape of the position sensor 44 body can be rectangular, cylindrical, or other suitable shape, including spherical, for example.

The fiducial F marker can be made of lead, tungsten, or the like. The fiducial F can be a spherical bead, for example, or a body having some other shape.

For ease of use, the shape of the self-calibrating device is not limited to a cube or box and the location of the fiducial marker is not restricted to the center of the top surface S2. According to an alternate embodiment of the present disclosure, more than one fiducial F is embedded in body 48. Fiducials F can be at different positions, such as at different heights, for example.

The sensor can be a high-resolution DR detector, such as a CCD (charge-coupled device), CMOS (complementary metal oxide semiconductor) or TFT (thin-film transistor) device, for example.

Use with DR Detector

Figure 7A:
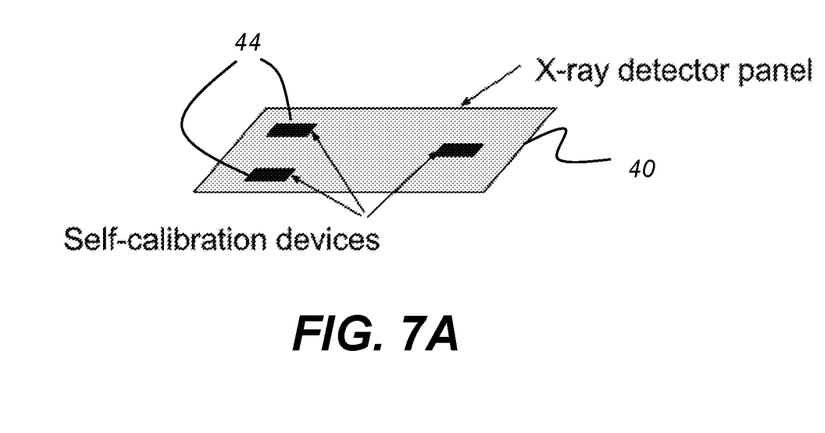
FIG. 7A is a perspective view that shows coupling of position sensors to a digital radiography detector.
Figure 7B:
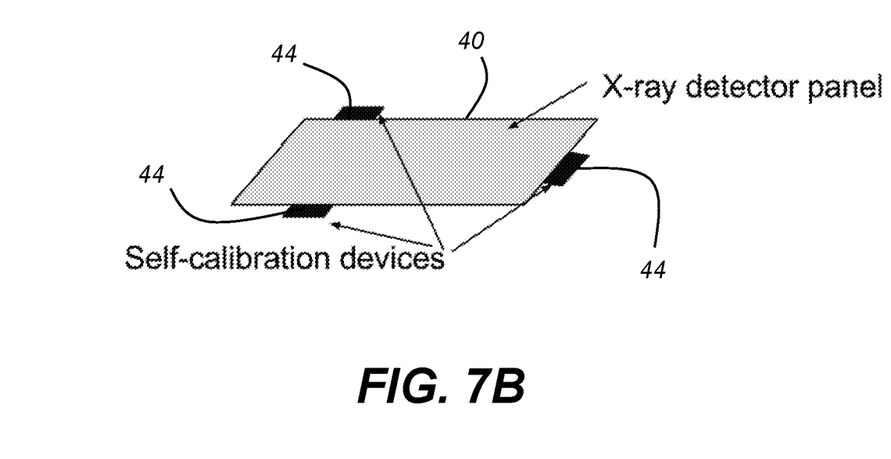
FIG. 7B is a perspective view that shows coupling of position sensors along edges of a digital radiography detector.

Position sensor 44 is coupled to DR detector 40, attached along edges of the detector 40 or at suitable positions behind the X-ray detector 40 panel. FIG. 7A shows position sensors 44 attached to the rear of the detector 40. FIG. 7B shows position sensors 44 attached along edges of detector 40. Various types of coupling methods and/or coupling hardware/member can be used to provide mechanical, adhesive, magnetic, detachable, fixed, or other coupling mechanism.

Figure 8:
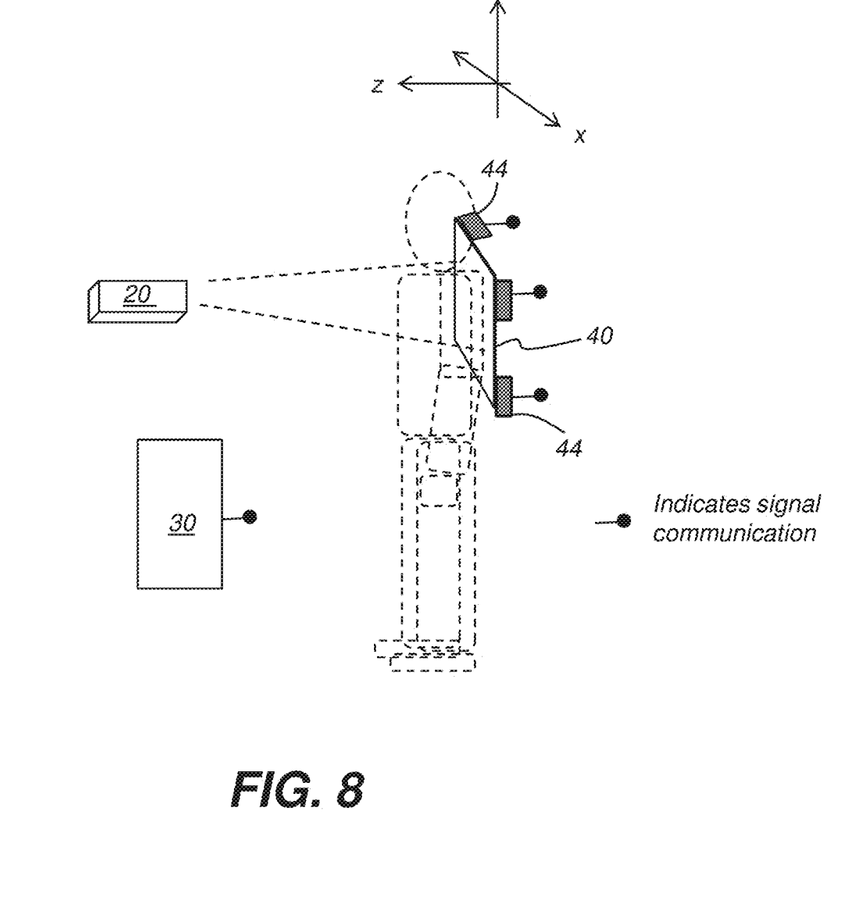
FIG. 8 is a schematic diagram that shows an apparatus for sensing position of an X-ray source to a digital radiography detector according to an embodiment of the present disclosure.

As FIG. 8 shows, position sensors 44 can be in signal communication with processor 30 for providing the needed image content for correlating the position of X-ray source 20 to DR detector 40. The signal from each position sensor 44 can be a wireless signal or can be provided using a wire, cable, or optical fiber connection. According to an alternate embodiment of the present disclosure, position sensors 44 are in signal communication with position sensing logic circuitry on the DR detector 40 itself, rather than with external processor 30. Power can be provided to the position sensors 44 from the DR detector, from an on-board battery, or from some other source.

With the self-calibrating position sensors 44 attached to the X-ray detector panel, the combined DR detector 40 device can be calibrated using a geometry calibration phantom. This allows computation of the relative position of the self-calibrating sensors 44 to the detector panel. This information can then be stored as part of metadata available with detector 40 or can be stored on processor 30.

According to an alternate embodiment of the present disclosure, position sensor 44 provides information that is used by positioning logic that executes as part of imaging apparatus 10 (FIG. 1). The positioning logic can provide a set of signals or displayed instructions for automated or manual movement of source 20 to a more suitable position for imaging, based on feedback data from position sensor 44.

According to an embodiment of the present disclosure, sensor element 34 of position sensor 44 lies in a plane that is parallel to the DR detector imaging plane. According to an alternate embodiment of the present disclosure, sensor element 34 can be embedded within a body of material at a tilted angle so that sensor 34 lies in a plane that is oblique to the imaging plane of the DR detector.

It is noted that there is typically a lead sheet or plate behind the X-ray detector 40 panel for reducing backscatter. To increase the exposure that is provided and to improve the accuracy of the self-calibrating position sensor 44 device, the DR detector can be designed with a removable shield portion of some type. For example, the DR detector 40 can be designed to allow a practitioner to temporarily open a window in the protective lead sheet backing of the DR detector 40 chassis in order to allow radiation access to the self-calibrating device. Alternately, position sensors 44 can be installed as an integral part of detector 40.

Sequence for Volume Image Reconstruction

Advantageously, the volume imaging apparatus can acquire and process calibration data as part of the sequence in which projection images are acquired and processed. The logic flow diagram of FIG. 9, applicable for tomosynthesis as well as for various types of CT imaging, shows a sequence for volume image acquisition and reconstruction using position sensors 44 coupled to DR detector 40. In a positioning step S910, the technician or other practitioner can manually position the DR detector 40 behind or beneath the patient or other subject and may manually position source 20 as needed. In an image acquisition step S920, at least one radiographic image of the subject is acquired. Simultaneously, a sensor acquisition step S930 can acquire image data for position detection from position sensor 44.

Figure 9:
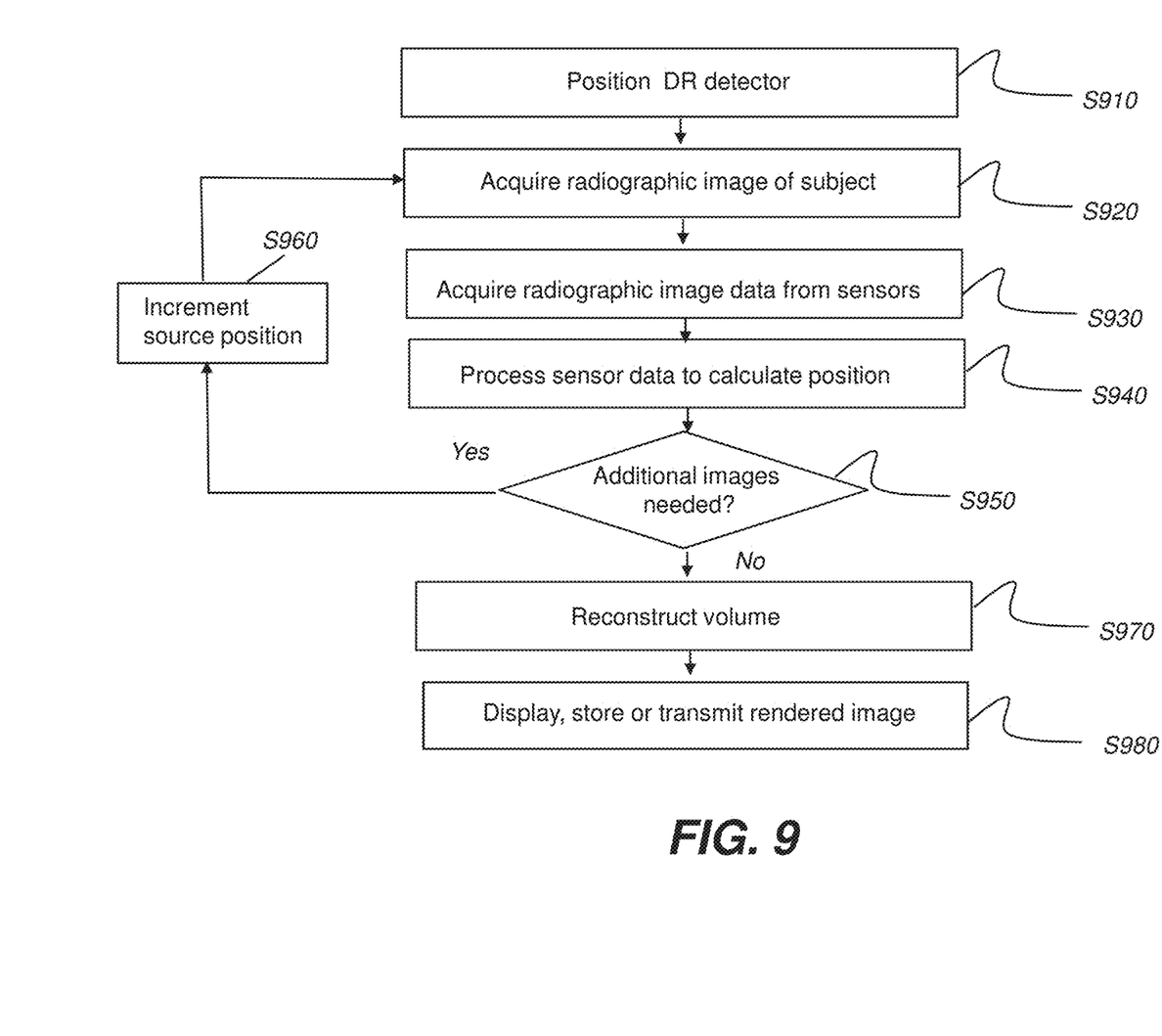
FIG. 9 is a logic flow diagram that shows an image acquisition and processing sequence for obtaining a volume image using the position sensor apparatus of the present disclosure.

A processing step S940 then processes the data acquired from position sensor 44 along with the image in order to calculate the relative position of source 20 to detector 40 during imaging. A test step S950 checks to determine whether or not all images needed for the volume reconstruction have been obtained. If additional images are needed to complete the series, a source indexing step S960 then translates the X-ray source 20 to the next position for imaging. Steps S920, S930, and S940 can be repeated until each image of the subject is acquired, along with accompanying information from sensors 44 for positioning calculation. A volume reconstruction step S970 then reconstructs the volume image content according to the projection images obtained. A display step S980 displays a rendering of the computed reconstruction, such as an image slice at a particular depth, for example. As part of display step S980, the volume image content can be stored or transmitted, such as over a network.

Advantageously, the position sensor 44 of the present disclosure can have different arrangements for different types of imaging systems. Multiple position sensors 44 can be used for ascertaining the position of the source with respect to a large detector. Position sensor 44 can be removable from DR detector 40, allowing substitution with a different type of sensor 44 that may use a different fiducial F, for example, or that may position fiducial F at a different distance from sensor element 34. This would allow, for example, the use of a first configuration of position sensor 44 for computed tomography (CT) imaging as well as the use of a second configuration for tomosynthesis imaging. A position sensor 44 can alternately be formed with two or more different types of fiducials, wherein each type of fiducial works best for a particular imaging modality. Referring to FIG. 5, fiducials F can be at different heights relative to sensor element 34.

Control logic of processor 30 can be programmed to enable or disable exposure and imaging for a particular type of imaging modality until measured data from position sensors 44 are within acceptable range.

Consistent with one embodiment, the present invention utilizes a computer program with stored instructions that control system functions for image acquisition and image data processing for image data that is stored and accessed from external devices or an electronic memory associated with acquisition devices and corresponding images. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A position sensor comprising:
   a radio-translucent body;
   one or more fiducials formed of radio-opaque material and disposed in or on the radio-translucent body;
   an area sensor element coupled to the radio-translucent body and spaced apart from the one or more fiducials at a fixed distance and energizable to acquire image content of the one or more fiducials during receipt of exposure energy from an X-ray source to generate a signal according to the acquired image content, wherein the sensor element is in signal communication with a processor energizable to generate data indicative of a position of the X-ray source relative to the position sensor; and a radio-opaque covering coupled against an outer surface of the radio-translucent body, wherein the position sensor is configured to be attached to and detached from an edge of a digital radiographic detector outside an imaging area of the digital radiographic detector and attached to and detached from a rear side of the digital radiographic detector.

2. The position sensor of claim 1 wherein the radio-translucent body is formed of a thermoplastic material.

3. The position sensor of claim 1 wherein the radio-opaque covering comprises a lead sheet or coating.

4. The position sensor of claim 1 further comprising a coupling mechanism to couple the position sensor to a radiography detector.

5. The position sensor of claim 1 wherein the sensor element is a CCD device.

6. The position sensor of claim 1 wherein the sensor element is a CMOS device.

7. The position sensor of claim 1 wherein the sensor element is a TFT device.

8. The position sensor of claim 1 wherein the position sensor has a single surface that is radio-translucent.

9. The position sensor of claim 1 wherein at least one of the one or more fiducials is spherical.

10. A method for sensing a position of a radiographic radiation source relative to a digital radiographic detector, the method comprising:

coupling two or more position sensors to the digital radiographic detector each at different locations on the digital radiographic detector, wherein each of the position sensors comprises a radio-translucent body, a radio-opaque fiducial disposed in or on the radio-translucent body, and an area sensor element coupled to the radio-translucent body, the two or more position sensors spaced apart from the fiducial at a fixed distance and energizable to acquire image content of the fiducial during receipt of exposure energy from the radiographic radiation source and to generate a signal according to the acquired image content, and wherein the area sensor elements are in signal communication with a processor energizable to generate data indicative of a position of the radiographic radiation source relative to the two or more position sensors;

directing radiation from the radiographic radiation source toward the two or more position sensors; and calculating a position of the radiographic radiation source relative to the digital radiographic detector according to the signals from the coupled two or more position sensors.

11. The method of claim 10 wherein coupling the two or more position sensors comprises coupling the sensors along different edges of the digital radiographic detector outside an imaging area of the digital radiographic detector.

12. The method of claim 10 wherein coupling the two or more position sensors comprises coupling the sensors each at a different location on a rear side of the digital radiographic detector relative to the radiation source.

13. An imaging system comprising:
an X-ray source;
a digital radiographic detector; and
two or more position sensors attached to the digital radiographic detector each at a different location, the position sensors each comprising:
a radio-translucent body;
one or more fiducials formed of radio-opaque material and disposed in or on the radio-translucent body; and
an area sensor element coupled to the radio-translucent body and spaced apart from the one or more fiducials at a fixed distance and energizable to acquire image content of the one or more fiducials during receipt of exposure energy from the X-ray source to generate a signal according to the acquired image content, wherein the sensor element is in signal communication with a processor energizable to generate data indicative of a position of the X-ray source relative to the position sensor.

14. The system of claim 13, wherein the two or more position sensors are configured to each be attached to and detached from a different edge of the digital radiographic detector outside an imaging area of the digital radiographic detector or each be attached to and detached from a different location on a rear side of the digital radiographic detector.

* * * * *